(12) United States Patent
Schwartz et al.

(10) Patent No.: US 8,702,685 B2
(45) Date of Patent: Apr. 22, 2014

(54) DRUG DELIVERY SYSTEM FOR TREATING ERECTILE DYSFUNCTION

(76) Inventors: Matthew Zane Schwartz, San Diego, CA (US); Robert Matthew Douglas, Oyster Bay Cove, NY (US)

(*) Notice: Subject to any disclaimer, the term of this patent is extended or adjusted under 35 U.S.C. 154(b) by 637 days.

(21) Appl. No.: 12/927,437

(22) Filed: Nov. 15, 2010

(65) Prior Publication Data

US 2011/0137114 A1 Jun. 9, 2011

Related U.S. Application Data

(60) Provisional application No. 61/261,369, filed on Nov. 15, 2009.

(51) Int. Cl.
*A61K 9/22* (2006.01)
*A61M 31/00* (2006.01)
*A61N 1/00* (2006.01)
*A61F 5/00* (2006.01)

(52) U.S. Cl.
USPC ............ 604/891.1; 604/503; 604/66; 600/38; 607/39

(58) Field of Classification Search
USPC ........ 604/890.1, 891.1, 892.1, 502–504, 511, 604/517, 65–67, 93.01, 131, 132, 140, 141, 604/143, 145, 151, 246, 248, 249, 604/288.01–288.04; 600/38–40; 607/39, 607/143
See application file for complete search history.

(56) References Cited

U.S. PATENT DOCUMENTS

| | | | |
|---|---|---|---|
| 4,664,100 A | 5/1987 | Rudloff | |
| 4,981,280 A | 1/1991 | Brandenberg | |
| 5,049,141 A | 9/1991 | Olive | |
| 5,085,656 A | 2/1992 | Polaschegg | |
| 5,215,088 A | 6/1993 | Normann | |
| 5,382,236 A * | 1/1995 | Otto et al. ................... | 604/141 |
| 5,551,849 A * | 9/1996 | Christiansen ................ | 417/472 |
| 5,575,770 A | 11/1996 | Melsky | |
| 5,643,207 A | 7/1997 | Rise | |
| 5,785,688 A | 7/1998 | Joshi | |
| 5,823,991 A | 10/1998 | Shim | |
| 6,679,832 B1 * | 1/2004 | Sultan ............................ | 600/40 |
| 6,885,895 B1 | 4/2005 | Whitehurst | |
| 7,276,057 B2 * | 10/2007 | Gerber ........................ | 604/891.1 |
| 7,865,243 B1 | 1/2011 | Whitehurst | |
| 7,890,177 B1 * | 2/2011 | Whitehurst et al. ........... | 607/39 |
| 2005/0273890 A1 | 12/2005 | Flaherty | |

OTHER PUBLICATIONS

MEDTRONIC, Synchromed/Isomed Implantable Systems Information for Prescribers. Jun. 2009.
The LEE Company, Lee Series 120 Solenoid Valve, May 2009.
NIH Consensus Development Panel on Impotence: Impotence JAMA. 270: 83. 1993.

(Continued)

*Primary Examiner* — Kevin C Sirmons
*Assistant Examiner* — Andrew Gilbert (57) ABSTRACT

Drug delivery systems, apparatus and methods to treat erectile dysfunction via an implanted drug infusion pump. The drug delivery system incorporates a passively pressurized drug infusion pump, one or more catheters, one or more microfluidic valves, a microcontroller, and one or more patient input mechanisms to deliver therapeutic solutions to the erectile tissues of a patient. The system in operation is entirely implanted and provides for moderated patient control over dosage via subcutaneously implanted input mechanisms, including in certain embodiments, neural control.

10 Claims, 9 Drawing Sheets

(56) References Cited

OTHER PUBLICATIONS

Dean RC, and Lue TF. Physiology of penile erection and pathophysiology of erectile dysfunction. Urol Clin North Am Nov. 2005: 32(4): 379.

Sattar AA. Salpigides G. Vanderhaeghen JJ. et al. Cavernous oxygen tension and smooth muscle fibers: relation and function. J Urol 1995: 154: 1736.

Brindley GS. Intrapenile drug delivery system. International Journal of STD & AIDS 7 (Suppl 3): 13-15 (1996).

Francois J. "Penile Injection Therapy—Treatment of Erectile Dysfunction (ED)." Penile prosthesis, penile implant, erectile dysfunction (ED), BPH, and urinary incontinence treatments (2008) J. Francois Eid MD—Web at http://www.UrologicalCare.com/other_ed_treatments/penile_injection_therapy/ Accessed on Nov. 13, 2009.

Steers WD. Neuroanatomy and neurophysiology of erection Sexuality and Disability, vol. 12, No. 1, 1994.

Steers WD, Mallory B, and de Groat WC. Electrophysiological study of neural activity in penile nerve of the rat. Am J Physiol Regulatory Integrative Comp Physiol. 254:989-1000, 1988.

* cited by examiner

DRUG DELIVERY SYSTEM FOR TREATING ERECTILE DYSFUNCTION

RELATED APPLICATION

This application claims priority to U.S. Provisional Application Ser. No. 61/261,369, filed Nov. 15, 2009, the disclosure of which is incorporated herein by reference.

BACKGROUND

The present disclosure relates to an implantable drug delivery system for the treatment of erectile dysfunction.

Erectile dysfunction ("ED"), sometimes called impotence, is the repeated inability to achieve or maintain an erection firm enough for sexual intercourse. The word impotence may also be used to describe other problems that interfere with sexual intercourse and reproduction, such as lack of sexual desire and problems with ejaculation or orgasm. ED can be a total inability to achieve erection, an inconsistent ability to do so, or a tendency to sustain only brief erections. In older men, ED usually has a physical cause, such as disease, injury, or side effects of drugs. Any disorder that causes injury to the nerves or impairs blood flow in the penis has the potential to cause ED. ED is treatable at any age, and awareness of this fact has been growing.

The penis contains two chambers called the corpora cavernosa, which run the length of the organ. A spongy tissue fills the chambers. The corpora cavernosa are surrounded by a membrane, called the tunica albuginea. The spongy tissue contains smooth muscles, fibrous tissues, spaces, veins, and arteries. The urethra, which is the channel for urine and ejaculate, runs along the underside of the corpora cavernosa and is surrounded by the corpus spongiosum. Erection begins with sensory or mental stimulation, or both. Impulses from the brain and local nerves cause the muscles of the corpora cavernosa to relax, allowing blood to flow in and fill the spaces. The blood creates pressure in the corpora cavernosa, making the penis expand. The tunica albuginea helps trap the blood in the corpora cavernosa, thereby sustaining erection. When muscles in the penis contract to stop the inflow of blood and open outflow channels, erection is reversed.

Current drugs for treating ED can be taken orally, injected directly into the penis, or inserted into the urethra at the tip of the penis. In 1998 the Food and Drug Administration approved sildenafil citrate (Viagra®, Pfizer, Inc.), the first pill to treat ED. Since that time, vardenafil HCl (Levitra®, Bayer Healthcare Pharmaceuticals, Inc.) and tadalafil (Cialis®, Eli Lilly & Co.) have also been approved. Additional oral medicines are being tested for safety and effectiveness. These drugs work by affecting certain parts of the signal pathway involved with penile smooth muscle relaxation, thus forcing smooth muscle relaxation and increasing the likelihood of achieving an erection.

Sildenafil citrate, vardenafil HCl, and tadalafil all belong to a class of drugs called phosphodiesterase (PDE) inhibitors. Taken an hour before sexual activity, these drugs enhance the effects of nitric oxide, a chemical that relaxes smooth muscles in the penis during sexual stimulation and allows increased blood flow. While oral medicines improve the response to sexual stimulation, they do not trigger an automatic erection, as injections do. Men who take nitrate-based drugs such as nitroglycerin for heart problems should not use PDEs because the combination can cause a sudden drop in blood pressure. Furthermore, taking a PDE inhibitor and an alpha-blocker, used to treat prostate enlargement or high blood pressure, at the same time can cause a sudden drop in blood pressure. And while these drugs are often effective in triggering the onset of an erection, they do not provide an immediate response to sexual stimulation. Additionally, drugs that are ingested orally require a total dose much larger than the minimal amount needed to stimulate the target site, resulting in side effects such as headache, facial flushing, upset stomach and sudden loss of vision. By utilizing a local drug delivery system, higher concentrations could be achieved at the target site even with the use of smaller dosages.

Oral testosterone can reduce ED in some men with low levels of natural testosterone, but it is often ineffective and may cause liver damage. Patients also have claimed that other oral drugs—including yohimbine hydrochloride, dopamine and serotonin agonists, and trazodone—are effective, but the results of scientific studies to substantiate these claims have been inconsistent.

Many men may achieve stronger erections by injecting drugs into the penis, causing it to become engorged with blood. Drugs such as prostaglandin E1, papaverine HCl, phentolamine, and alprostadil (Caverject®, Pfizer, Inc.) have been used for this purpose. For example, alprostadil induces erection by relaxation of trabecular smooth muscle and by dilation of cavernosal arteries. This leads to expansion of lacunar spaces and entrapment of blood by compressing the venules against the tunica albuginea, a process referred to as the corporal veno-occlusive mechanism. A major drawback of these therapies is that a patient must inject these drugs directly into the penis immediately prior to sexual intercourse, in addition, repeated administration may result in scarring.

A system for inserting a pellet of alprostadil into the urethra is marketed as Muse® (Vivus, Inc.). The system uses a prefilled applicator to deliver the pellet about an inch deep into the urethra. An erection will begin within 8 to 10 minutes and may last 30 to 60 minutes. Common side effects are aching in the penis, testicles, and area between the penis and rectum; warmth or burning sensation in the urethra; redness from increased blood flow to the penis; and minor urethral bleeding or spotting. Like the injection therapies, a major drawback is that the application of the pellet must take place immediately prior to sexual intercourse.

External mechanical vacuum devices may be used to cause an erection by creating a partial vacuum, drawing blood into the penis, engorging and expanding it. These devices are typically only marginally effective and their use can cause embarrassment to the patient.

Surgery is sometimes employed as a treatment for ED, and usually has one of three goals: to implant a prostheses; to reconstruct arteries to increase flow of blood to the penis; or to block off veins that allow blood to leak from the penile tissues.

Mechanical prosthetic implants can simulate an erection in many men with ED. Several designs are currently employed, including one design that uses balloon-like chambers implanted within the penis, a small fluid reservoir implanted within the body and a manual pump mechanism implanted in the scrotum, which drives fluid from the reservoir to the chambers, thereby simulating an erection. Malleable implants usually consist of paired rods, which are inserted surgically into the corpora cavernosa. The user manually adjusts the position of the penis and, therefore, the rods. Adjustment does not affect the width or length of the penis. Drawbacks of implants include mechanical breakdown and infection, the need for fairly invasive surgery, damage to previously-intact penile tissue, and the fact that the erection achieved is not physiologically natural, i.e., not caused by blood pressure and blood volume changes within the penile tissues, resulting in a hindered sexual experience.

Surgery to repair arteries can reduce ED caused by obstructions that block the flow of blood. The best candidates for such surgery are young men presenting with discrete blockage of an artery, usually due to an injury to the crotch or fracture of the pelvis. The procedure is almost never successful in older men with widespread blockage. Surgery to veins that allow blood to leave the penis usually involves an opposite procedure—intentional blockage. Blocking off veins (ligation) can reduce the leakage of blood that diminishes the rigidity of the penis during erection. However, experts have raised questions about the long-term effectiveness of this procedure, and it is rarely performed.

Each of these methods treat ED to varying degrees, but each has their drawbacks such as systemic side effects, poor response times, cumbersome or painful delivery mechanisms, need for traumatic surgery and physiologically unnatural results. In addition, many of these methods are unable to achieve a physiologically natural erection and all require at least some amount of, and sometimes significant, pre-intercourse intervention.

SUMMARY

Recognition of a need for an improved form of therapy for ED led to the development of the low-power implantable drug delivery system described herein. The device uses a passively pressurized drug reservoir, the flow from which is modulated by ultra-low power microfluidic valves under direct or indirect control of the patient. The system provides for the delivery of a precise dosage of an erection-inducing pharmaceutical agent directly to the target tissue.

The low power consumption of the described device is achieved, in part, by the use of a passively-pressurized propellant chamber within the drug infusion pump portion of the device as the primary driving force for fluid flow. Such implantable constant-flow infusion pumps are well-known in the art (see, e.g., U.S. Pat. No. 5,643,207), and typically rely on a liquid/vapor equilibrium at physiologic temperature to maintain a constant pressure on the drug, which is housed in a compartment separate from, but adjacent to, the propellant chamber. The prior art teaches that, by selecting an appropriately-sized capillary tube to restrict fluid flow of the drug, a chosen constant flow rate can be maintained over long periods of time, often measured in months or years. Using passive pressurization to drive fluid from the drug reservoir requires no battery power, making it ideal for long-term therapeutic use in an implanted device, but conventional devices according to the prior art designs are not able to administer a discrete bolus of therapeutic upon command.

The present invention incorporates the use of microfluidic control valves, allowing for an ultra-low-power implantable device that can maintain therapeutic effectiveness over the course of many years, and many discrete drug bolus administrations. The incorporation of microfluidic control valves and a microcontroller allows for the use of what would otherwise be a constant-flow pump in an application requiring discrete and precise dosages at varying time intervals. In addition, microfluidic valves allow for more precise fluid flow regulation, and therefore, dosages.

The system described also incorporates a control module that allows both patient control over dosing, as well as prevention of accidental dosage administration, avoiding overdose. Implementation of patient control input may be accomplished through the use of implanted subcutaneous buttons, implanted subcutaneous RFID tags, an implanted neural signaling interface, RF triggers or any combination of these or similar input mechanisms. For a neural signaling interface, neural signals may be registered via microelectrodes in electrical communication with the spinal cord, brain, spinal nerves, cauda equina, or peripheral nervous system. Such signals can then be processed by a microcontroller and, under certain conditions, be used to trigger release of the therapeutic. Neural signals may thus be used, either alone or in combination with other control mechanisms, to achieve an essentially natural physiologic response to sensory or mental stimulation.

While there have been prior attempts to devise an implantable erection assist apparatus, see, e.g., U.S. Pat. No. 5,823,991 to Shim, such devices suffered from high power requirements because such devices taught actively pumping the therapeutic, distinctly limiting the useful life of the implanted device. In addition, such devices did not provide for a seamless, completely implanted user-interface control mechanism. The present invention overcomes these shortcomings.

The device and methods described herein result in increased treatment effectiveness, smaller effective dosages and reduced side effects as compared to the prior art. By delivering vasodilating compounds directly to the corpus cavernosum, without requiring systemic ingestion or local injection of active compounds, and especially when under neural control, the described device and method results in an essentially physiologically natural response to stimulation.

These general and specific elements can be implemented in a variety of combinations as apparatuses, methods, and systems. The details of one or more implementations are set forth in the accompanying drawings and the description below. Further features, aspects, and advantages will become apparent from the description, the drawings, and the claims.

BRIEF DESCRIPTION OF THE DRAWINGS

Like reference symbols indicate like elements throughout the specification and drawings.

DETAILED DESCRIPTION

Figure 1:
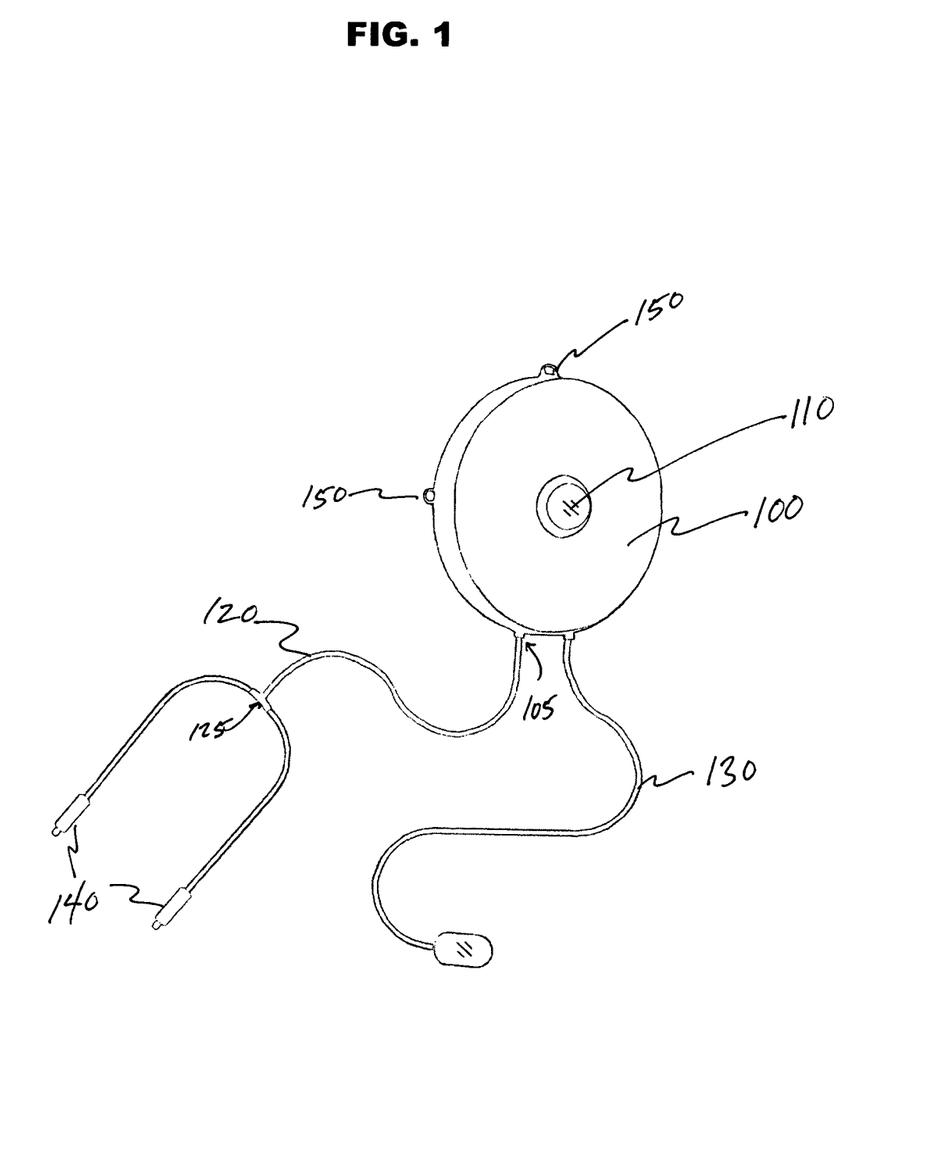
FIG. 1 depicts a housing with an integrated pump and control mechanisms according to one embodiment of the invention.

The overall system described herein comprises a passively pressurized drug infusion pump, microfluidic valves, catheters, a microcontroller, patient input mechanisms and a power source. In a main embodiment, the system comprises one or more drug fluid reservoirs to store a pharmaceutical agent effective for treating ED; one or more passively-pressurized chambers in pressure communication with the drug fluid reservoir(s); one or more catheters to transport the pharmaceutical agent to the penis, more specifically, to the corpora cavernosa on one or both sides of the penis; one or more low-power microfluidic valves for occluding flow of the pharmaceutical agent; a patient input mechanism; a microcontroller unit for (i) interpreting input from the patient input mechanism, (ii) controlling the microfluidic valves, thereby triggering the release of the dosage, (iii) performing any necessary computational functions, and (iv) accepting programming instructions from a user; and a power source. The fluid reservoirs, pressurized chambers, microcontroller, and power source may be housed within a single structure 100, as depicted in FIG. 1. FIG. 1 also depicts a drug reservoir fill port 110, a drug administration catheter 120, an implantable patient input mechanism 130, microfluidic valves 140, and housing attachment points 150.

Figure 2:
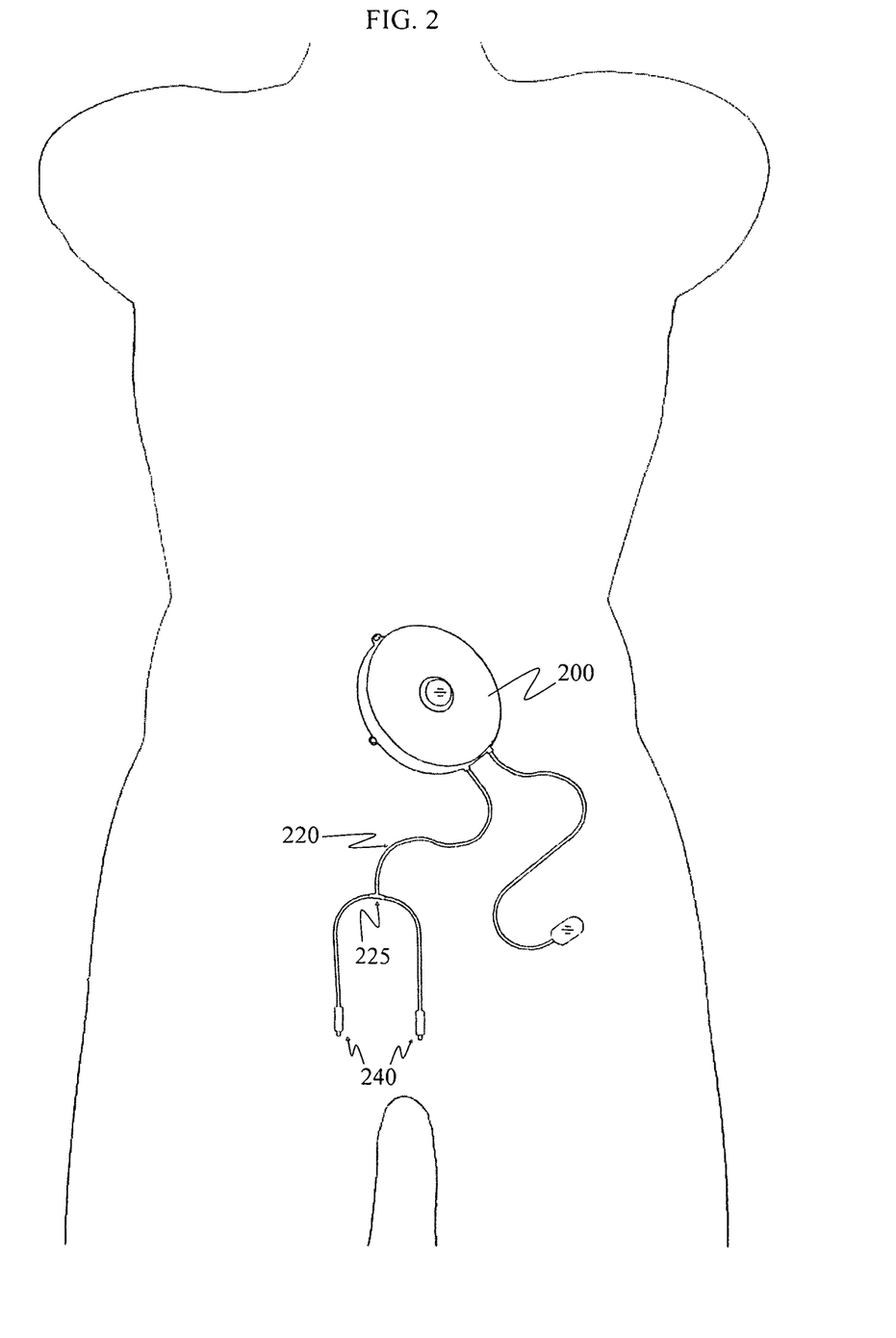
FIG. 2 depicts one potential placement of the device housing within a patient, with catheters placed to deliver the selected drug.

In one embodiment, the device housing 100 is designed to fit congruently within the contours of a patient's pubic bone. In another embodiment the device housing 100 is implanted in the subcutaneous tissue of the abdomen, implantation is preferably done via a minimally invasive procedure. FIG. 2 depicts a potential arrangement of the device housing 100, catheters 120 and patient input mechanism 130 within a patient. As patients will have differing pubic bone structures, in one embodiment, the contours on the posterior surface of the device housing 100 may be selected from different undersurfaces that can be attached to the housing prior to surgical implantation of the device. In a typical embodiment, the outer shell of the housing 100, and any attached undersurface, will be constructed of titanium or a titanium alloy such as niobium and tantalum. Although the device housing 100 is not limited to titanium and its alloys, such materials are ideal for, and conventionally employed as exterior surfaces for, hermetically sealed implantable devices. In one embodiment, the device housing 100 will have a curvaceous surface to reduce the device profile, ideally with virtually no sharp edges.

Figure 3:
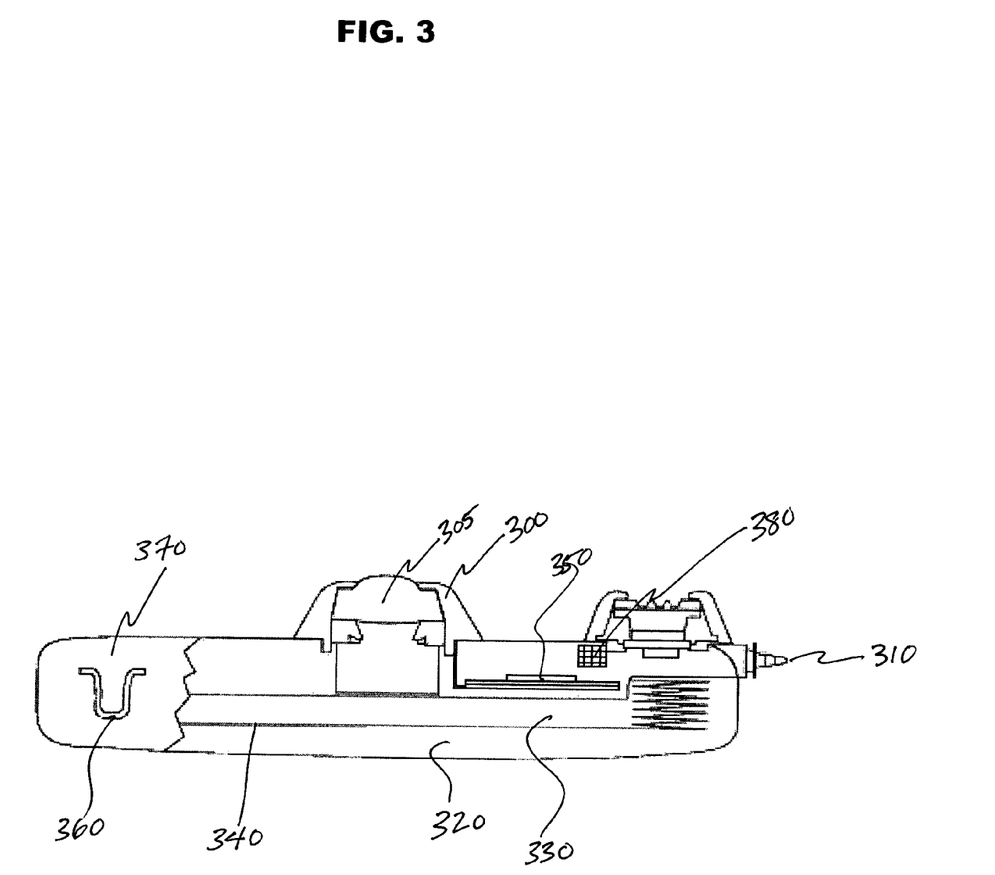
FIG. 3 presents a cutaway view of a constant flow infusion pump of a type that may be employed in the invention.

In accordance with one aspect of the invention, a constant-flow, passively-pressurized drug infusion pump of essentially standard construction may be employed within the device housing to provide the driving force for discharge of the therapeutic drug to the intended administration site. In one embodiment, as shown in FIG. 3, the infusion pump will provide a drug reservoir containing the selected therapeutic in solution, wherein the reservoir is in pressure communication with a passively-pressurized propellant chamber. In accordance with known practice, a fluorocarbon gas may be used to create the specific pressure necessary for expelling solution from the drug reservoir; trichlorofluoromethane (Freon) is a typical choice that vaporizes at physiologic temperatures. FIG. 3 depicts a typical constant-flow, passively-pressurized drug infusion pump of the type well-known in the art, e.g., as described in U.S. Pat. Nos. 3,731,681 and 4,221,219.

In one embodiment, the infusion pump portion of the disclosed device is composed of the following components: a collapsible drug reservoir of a selected initial volume 330; propellant (pump drive) chamber 320; reservoir fill port incorporating a self-sealing septum 300; a biocompatible housing 370; capillary tubing 380 and housing attachment points for securing the housing via fixation devices and/or sutures 360. A pump in accordance with this general design has a constant flow rate that is selected by design choices regarding the volume of the drug reservoir 330, size and length of capillary tubing 380 and internal pressure in propellant chamber 320.

In accordance with the embodiment depicted in FIG. 3, the propellant chamber 320, located behind the drug reservoir 330, is filled with a two-phase fluid that has a significant vapor pressure at body temperature and places a constant pressure on the drug reservoir 330 to force the drug out through the catheter port 310 to the site of delivery via a capillary (not shown). As the fluid vaporizes at body temperature, it compresses a bellows 340 separating the drug reservoir 330 from the propellant chamber 320, and urges the contents of the reservoir 330 to the administration site. In one embodiment of the infusion pump, the pump housing is separated into two chambers by a flexible titanium bellows 340. In this embodiment, the propellant chamber 320 is a sealed compartment that contains a two-phase (liquid-vapor) propellant. The vapor pressure of the propellant exerts pressure on the bellows 340, which is communicated to drug reservoir 330, forcing the therapeutic solution from the reservoir 330, optionally through a filter 350, and optionally through a capillary flow restrictor 380, out of the pump via an outlet 310, through a catheter (not shown) to the intended site within the body.

In accordance with known technique, the flow rate may be varied by using different lengths and/or diameters of flow restrictive capillary tubing. For a given diameter, the flow rate is directly proportional to the length of the tubing, increasing the length increases the fluid flow restriction resulting in a slower flow rate, while decreasing the length reduces flow restriction and increases the flow rate.

In a typical embodiment, such as that depicted in FIG. 3, the housing 370 encloses a collapsible drug reservoir 330, with an initial internal volume of, for example, 20 ml, or in other embodiments, with an initial internal volume of 35 ml or 60 ml; other volumes may also be selected, limited only by the requirement that the overall size of the housing 370 must allow for implantation. Depending on the size of the drug reservoir 330 selected, the housing 370 may range in thickness, for example from 0.67 inches to 1.2 inches, and may be approximately three inches in diameter.

In accordance with basic implantable pump technology, the drug reservoir 330 may be refilled periodically and can be accessed transcutaneously by means of a reservoir fill port 300 disposed on the surface of the device housing 370. In one embodiment, in accordance with known techniques, a stressed elastomeric seal 305 may be punctured with a specially shaped needle (not shown). For example, in one embodiment, the drug reservoir can be refilled by inserting a non-coring needle through the skin of the patient and through a septum, e.g., a silicone septum, to allow additional drug to be delivered to the drug reservoir from outside the patient's body. In one embodiment, the drug reservoir fill port 300 is raised from the outer surface of the device housing 370 such that a clinician can palpate the port 300 from the surface of a patient's body to identify the location and orientation of the port 300. In an optional embodiment, the drug reservoir port includes an internal needle stop structure 380 intended to limit the needle's travel and to prevent damage to the drug reservoir 330. Refilling the drug reservoir also recharges the pressure within the propellant chamber 320, as the change in propellant chamber volume recondenses vapor within the propellant chamber 320.

Figure 4:
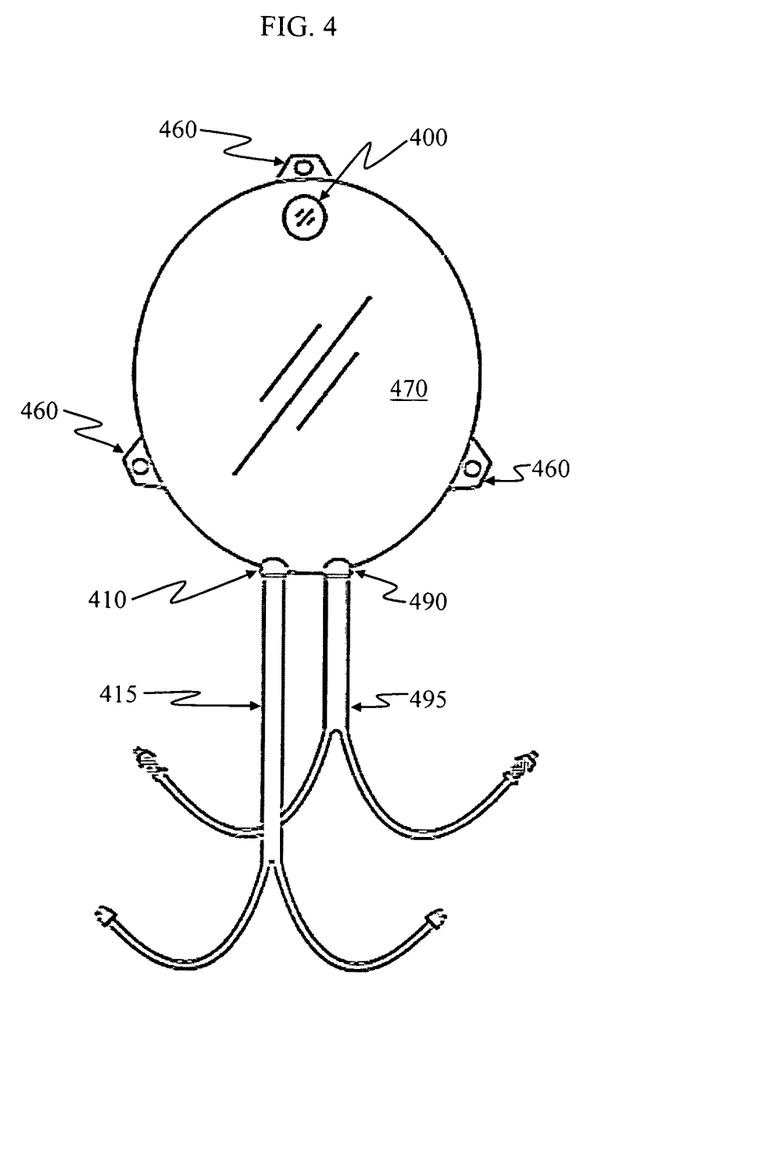
FIG. 4 depicts a frontal view of one embodiment of the device.

In one embodiment, as depicted in FIG. 4, the housing 470 has three orifices, one for a catheter outlet 410, one for an electrode input 490, and one for the reservoir fill port 400. Referring to FIG. 4, the catheter port 410 and electrode port 490 are situated towards the inferior anterior face of the device so a surgeon can easily guide the catheters 415 to the corpora cavernosa and the electrodes 495 to either the cavernous or dorsal nerves of the penis. The refillable port 400 is located on the anterior side of the device. In one embodiment, the port 400 is closed off to the environment by a compressible stage that when penetrated allows a fluid inflow; in this embodiment, the opening of the port will direct a specialized needle into a one-way valve that connects to a refillable drug reservoir bladder. When removing the drug delivery syringe, the compressible stage will return to its original state, sealing the device from the exterior environment.

Figure 5A:
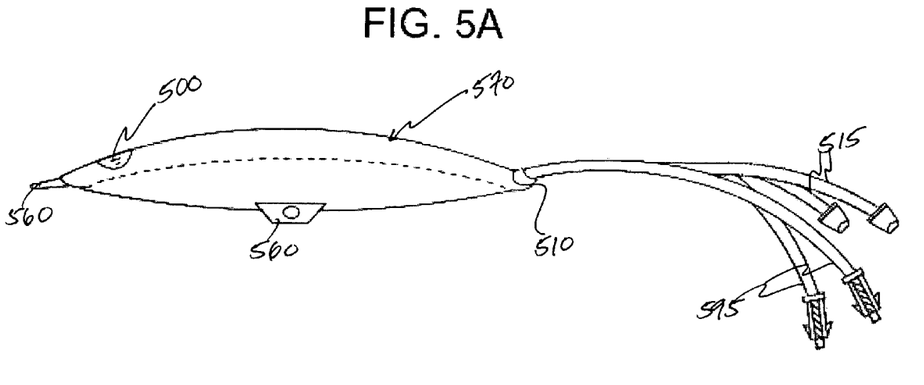
FIG. 5 depicts a side view of one embodiment of the device.
Figure 5B:
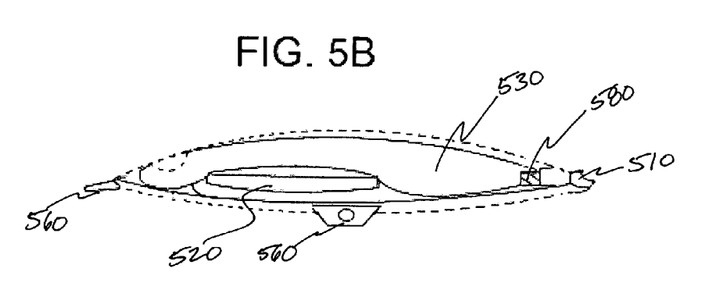

FIG. 5A depicts such a drug reservoir fill port 500 in housing 570. FIG. 5A also depicts a side-view of one embodiment of the invention, including catheter outlet port 510, catheters 515, electrodes 595 and housing attachment points 560. FIG. 5B depicts a cut-away view of the same embodiment, illustrating a catheter outlet port 510, a propellant chamber 520, a drug reservoir 530, attachment points 560 and housing 570.

Securing the housing of the device within the abdomen of the patient may be accomplished in multiple ways. Ideally, the device will be secured subcutaneously within the abdomen of a patient via a minimally-invasive procedure. The body of the device may be constructed to have one or more attachment points along its circumference, such as depicted at 360, 460 and 560. These attachment points would allow for securing the device to supporting tissue structures with the abdomen of a patient, for example, via sutures or other fixation devices. In an alternative embodiment, the attachment points could be oriented so that the device could be attached to the pelvic bone via standard fixation devices, for example, screws, disposed through the attachment points and secured into the underlying bone. In an alternative embodiment, the attachment points, such as those depicted at 360, 460 and 560 could be adapted such that the device may be fixed either to bone or tissue structures via sutures. The precise placement of the device is left to the discretion of the clinician; the election of a particular fixation technique does not impact the invention.

The use of a microfluidic valve to control flow from a constant flow rate infusion pump, such as the above-described pump embodiments, results in reduced size and power requirements as compared to the prior art. Miniature, magnetically latched, solenoid valves allow for high-performance flow switching characteristics, requiring only a momentary (for example, 1 ms) voltage pulse to switch the valve state. Microfluidic valves that provide reliable bi-stable performance, with minimal power drain are readily commercially available, for example, the Series 120 Solenoid Valve available from The Lee Co. (Westbrook, Conn.), part # LFLX0510200B.

Valves to be used in the described system must be biocompatible and preferably allow only unidirectional flow. In accordance with the invention, the selected valves should require very little power to operate, thereby extending the effective implanted life-span of the system to a therapeutically useful duration. One of skill in the art may select from a number of available microfluidic valves, for example from commercially-available microfluidic solenoid valves, in accordance with these criteria. In one embodiment, the valves 140 are disposed at the distal end(s) of the catheter(s), as depicted in FIG. 1, in an alternative embodiment, the valves are disposed within, or adjacent to, the pump housing 100.

The selected therapeutic drug is delivered from the pump housing to the site of administration via one or more biocompatible catheters 120. In one embodiment, the catheter will exit the pump housing via a single port 105, and include a Y-junction 125 so that each of the cavernosal bodies will be in fluid communication with the pump and receive the therapeutic drug. In order to prevent external forces from compressing the catheters and thus causing unwanted dosages to escape, the catheters may be reinforced with a rigid internal structure, such as a titanium inner coil. In addition, the catheters may be adapted to carry electrical signals from the microcontroller to the distal valves, for example, via an embedded insulated wire.

Implantation of the device housing 200 in close proximity to the pubic bone puts the device in an excellent location for extending the drug delivery catheters 220 to the corpora cavernosa, as depicted in FIG. 2. In the preferred embodiment, there are two catheters 220, one each for the left and right corpora cavernosa, and each catheter tip may be secured to the base of the corporal bodies using small sutures. The placement of the distal ends of the catheters is a matter of preference for the surgeon performing the implantation, but it is to be expected that smooth muscle dilation at the very base of the corpora cavernosa will result in the greatest increase in blood flow as the penile arterioles are largest before they enter the shaft of the penis.

Optionally, the catheters 220 and valves 240, if situated at the distal end of the catheters, may be coated with one or more compounds to reduce one or more of: host immune response, blood coagulation at the catheter outlet, or the growth of a tissue mass which might occlude the catheter outlet. In addition, the catheters may be coated internally with a substance that prevents particulate build up. A third microfluidic valve may be installed in-line with the catheter 120, upstream (proximal to the housing) of the Y-junction 125 to be used as a fail-safe mechanism. In accordance with this aspect, if the microcontroller senses that one or both of the distal-end microfluidic valves have remained open beyond the specified duration, the third, upstream valve will be triggered to close, thereby preventing a free-flow situation and overdose. In a similar embodiment, four valves may be provided: two distal valves 140 under normal operational control of the microprocessor as described above to allow dosage, and two fail-safe valves (not shown), each disposed in close proximity, and within the fluid path, to each distal valve 140. These fail-safe valves are ordinarily open, allowing fluid flow, but can be shut by the microcontroller when a malfunction of the distal valves 140 is detected.

The system of the invention also provides for input by the patient in order to either trigger release of therapeutic or to arm the system prior to initiating the drug delivery process. In an embodiment where a single control input by the patient is sufficient to trigger drug delivery, any one of a number of typical control input mechanisms may be implanted. For example, the system could register patient input via an implanted subcutaneous button, via an implanted subcutaneous RFID tag or reader, or via other non-invasive communication method including, but not limited to, capacitive touch sensor, vibration sensor, RF control module, or chemical sensor.

Figure 6:
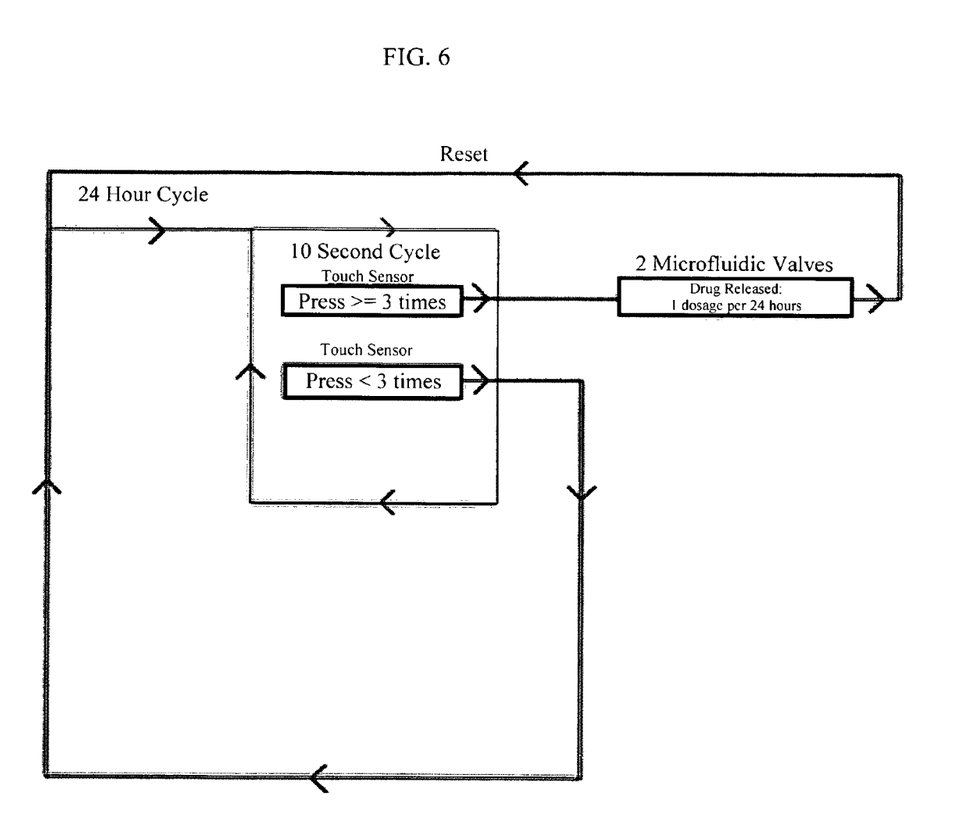
FIG. 6 represents one possible configuration of microcontroller logic based on user input.

In one embodiment, in order to prevent accidental dosage, a subcutaneous implanted button would require a specific sequence of presses before the microcontroller allows release of the therapeutic. In an exemplary embodiment, as depicted in FIG. 6, the subcutaneous button would have to be pressed three or more times within ten seconds. In other embodiments, two or more patient input mechanisms must be initiated prior to release of a therapeutic. For example, in one embodiment, an RFID tag keyed to the system may be used to 'arm' the system prior to a second patient input, for example, neural input or a button press sequence, the second input registered would then trigger release of the therapeutic. In a preferred embodiment, further user input is filtered out for a period of time after successful administration of therapeutic, thereby preventing overdose and preserving battery life.

Figure 7:
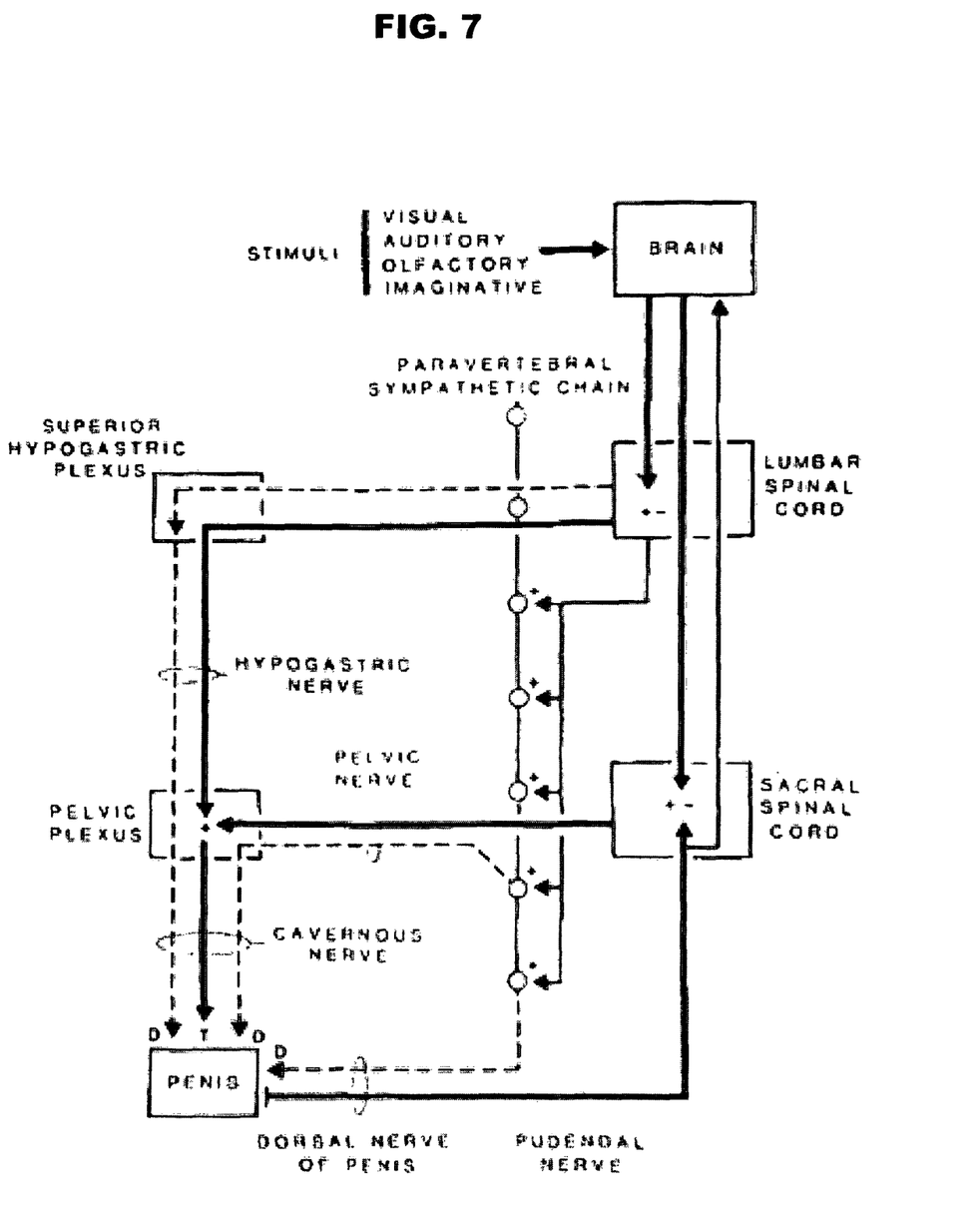
FIG. 7 is a block diagram depicting the nervous system control that leads to stimulation or inhibition of erection.

Within the scope of the invention is neurological interfacing, whereby implanted microelectrodes monitor the endogenous neural activity of, for example, the nerves related to the penis. In one embodiment, the microcontroller will analyze the registered action potentials, and the system will release therapeutic in response to signals indicating a sufficiently high state of stimulation. Penile innervation involves both the autonomic and somatic nervous systems; the sympathetic and parasympathetic nervous systems are contained in the cavernous nerves. FIG. 7 is a block diagram depicting the nervous system control that leads to stimulation or inhibition of erection. The cavernous nerves enter the corpora cavernosa and are primarily responsible for the neurovascular events of both erection and detumescence. Somatic innervation of the penis, achieved with the dorsal nerve, is responsible for sensory function and conscious contraction of the local muscles. The autonomic innervation of the penis stems from the pelvic plexus. Branches from the pelvic plexus also innervate the rectum, bladder, prostate and sphincters. These autonomic pathways are responsible for carrying the cerebral impulses to signal erection. There is also evidence that a reflex involving the somatic pathways can stimulate erection without cerebral processing. Through the use of microelectrodes in electrical communication with selected nerves, a patient's own natural neural signals can be sent as an input to the microcontroller. When the nervous signal matches that of true sexual stimulation for a preset period of time, the microcontroller may then trigger release of a predetermined dosage. In one embodiment, the system must be armed, by patient input, prior to monitoring neural activity for stimulatory signals.

In one embodiment, the cavernous nerves are used as the input source because they transmit signals from the brain that are meant to trigger erection. By intercepting and interpreting these signals, the system of the invention can trigger the release of therapeutic directly into the corpora cavernosa based on endogenous bioelectrical activity intended to cause an erection. Unfortunately, the cavernous nerves may be difficult to access because they are located in very close proximity to the prostate and bladder, and they are not located in a location readily accessible from the typical initial surgical incision. Despite these drawbacks, for a given patient it may be possible for the surgeon to laparoscopically position the electrodes in the correct location.

In another embodiment, by intercepting signals from the dorsal nerves, release of vasodilator can be triggered by signals that are sensory in nature. For example, if the cavernous nerves are either damaged or inaccessible, or in a case where the patient's central nervous system is incapable of transmitting a signal intended to cause an erection, the physician will still be able to use the device in connection with the dorsal nerves. These nerves are located very close to the pubic bone and are fairly large in size. The dorsal nerves carry sensory signals from the shaft of the penis to the spinal cord and eventually the brain for interpretation; physical stimulation to the penis of a sexual nature will drive a strong sensory response transmitted via the dorsal nerves.

In an alternative embodiment, both cavernous and dorsal nerves are monitored. In any embodiment, the decision of whether to attach the electrodes to the dorsal or cavernous nerves is contingent on patient specific etiology of ED and accessibility of the nerves; the system described herein may be implanted in the manner most appropriate for the presentation of disease in a specific patient. Electrodes appropriate for use in the disclosed invention are well-known in the art, see, e.g., U.S. Pat. No. 5,215,088, although other electrode designs may be employed with the instant invention; systems for interpretation of neural signaling and control of devices are also well known, see, e.g., U.S. pat. pub. no. 2005/0273890, both of which are incorporated herein by reference.

Using endogenous neural activity as a trigger for system release of the selected therapeutic provides the most physiologically restorative treatment, as the patient will not be consciously aware of the signal triggering release of the therapeutic.

In accordance with the invention, when a preset level of stimulation is registered by the microcontroller for a preset length of time, drug release will be triggered. Interpreting the neural signal characteristics that should trigger drug release is governed by the fact that peripheral nerve action potentials have very consistent shapes, and that the level of stimulation is directly proportional to the frequency of action potentials rather than to the voltage amplitude or duration of the action potentials. Therefore, the key indicator of intercepted neural activity that sexual stimulation is occurring is a high threshold frequency. Animal studies (see, e.g., Steers W D, et al. Am J Physiol. 254:989-1000 (1988), incorporated herein) confirm that increased frequency of action potentials corresponds with increased level of stimulation. During the study, the frequency never exceeded 250 Hz; this equates with a period of 4 ms. As 4 ms is approximately the refractory period of peripheral nerve action potentials, regardless of the level of stimulation, a frequency of 250 Hz cannot be exceeded. This same study found that during sexual stimulation the frequency of action potentials in rats was approximately 200 Hz. Based on this, the microcontroller can be programmed to register activity in the range of 150 to 250 Hz, more particularly 150 to 200 Hz, or in some embodiments approximately 200 Hz, as sufficient to register as sexual stimulus as opposed to normal nervous activity. In one embodiment, the microcontroller of the invention is programmable such that the threshold frequency for registering as a sexual stimulus may be modified by a clinician in response to a particular patient's needs, or in response to further human clinical study. For example, if the patient is incapable of achieving an erection due to the lack of a sufficient brain-stimulated impulse, then the microcontroller may be configured to have a lower frequency threshold for registering a sexual stimulus.

Figure 8:
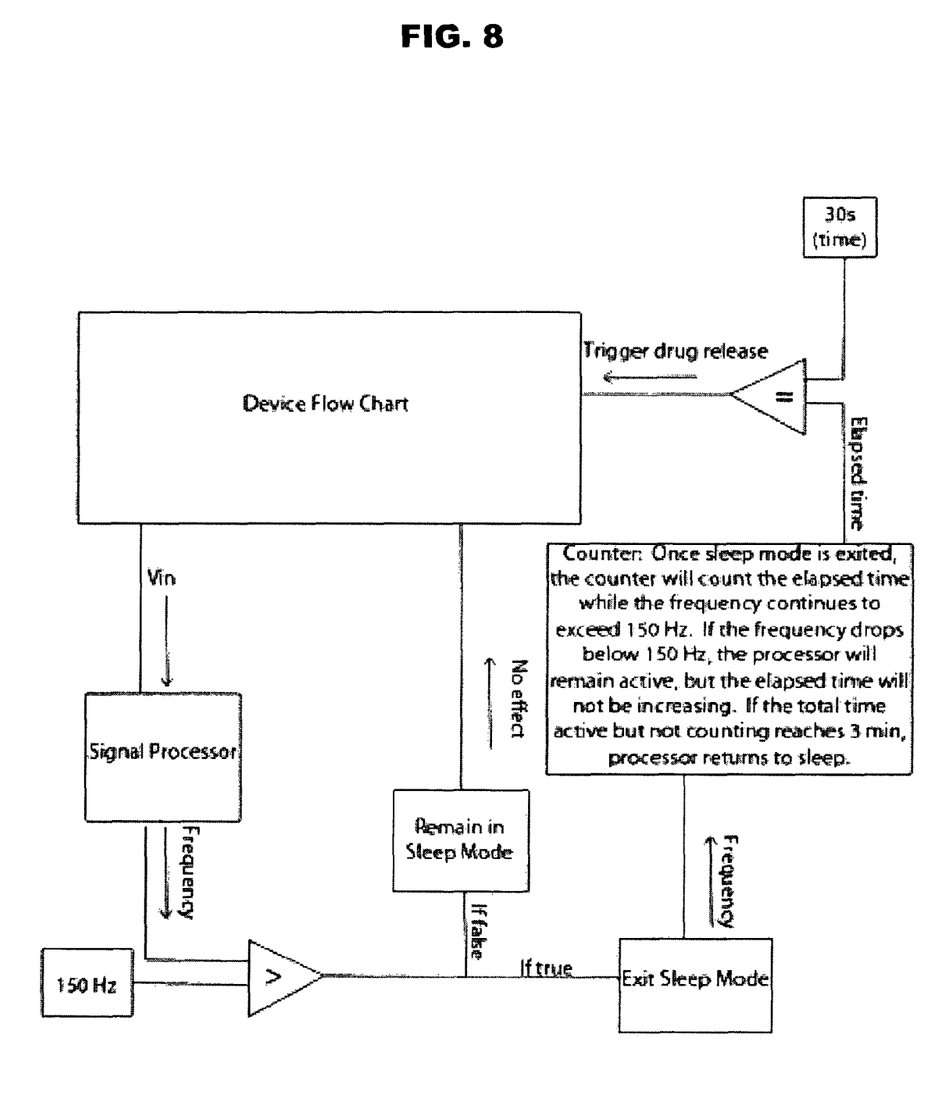
FIG. 8 is a block diagram depicting a method for microcontroller control of drug release based on exemplary neural threshold stimulation and duration values.

In accordance with this aspect of the invention, the microcontroller must also measure the duration of the registered sexual stimulus prior to triggering drug release. In one embodiment, the microcontroller is programmable to allow the clinician to select the appropriate duration of a registered sexual stimulus prior to drug release. In one embodiment, for example, the duration of registered sexual stimulus must exceed 30 seconds in order to trigger drug release. In another embodiment, registered sexual stimulus must exceed 1 minute in order to trigger drug release. In one embodiment, as depicted in FIG. 8, the microcontroller will be in a low-power "sleep mode" during periods without sexual stimulation. In such an embodiment, when a sexual stimulus of appropriate threshold frequency is detected, the microcontroller will record the amount of time that the signal frequency is greater than the selected threshold. In one embodiment, if the total time of stimulation does not amount to the selected duration threshold, for example, 30 seconds, within a certain time window, for example, 3 minutes, the sexual stimulus duration counter will reset to zero, and the microcontroller will return to "sleep mode." If the sexual stimulus duration counter does reach the selected duration threshold during the defined time window, then the drug administration will be triggered. In one embodiment, the microcontroller will be forced to remain in "sleep mode" for a certain period after triggering drug release. This refractory period may be set at any arbitrary time period, including about 24 hours, to prevent recurring drug administration, including drug overdose.

A standard microcontroller may be programmed to provide control over the drug delivery system. The invention, however, is not limited to any particular computational unit; the only requirement is for a robust, biocompatible, low-power unit that can perform the various recited functions. The microcontroller may be responsible for determining what is considered a sexual stimulus, and maintaining a refractory period post-administration, both as described above, as well as monitoring the quantity of drug in the drug reservoir, controlling the microfluidic valves, including any shut-off valve(s), and interpreting signals from the patient input mechanism(s). The microcontroller may also be programmed to calculate the volume of therapeutic remaining within the drug reservoir by summing and storing the amount of therapeutic administered in each dosage administration, or alternatively, by monitoring pressure changes within the drug reservoir.

Figure 9:
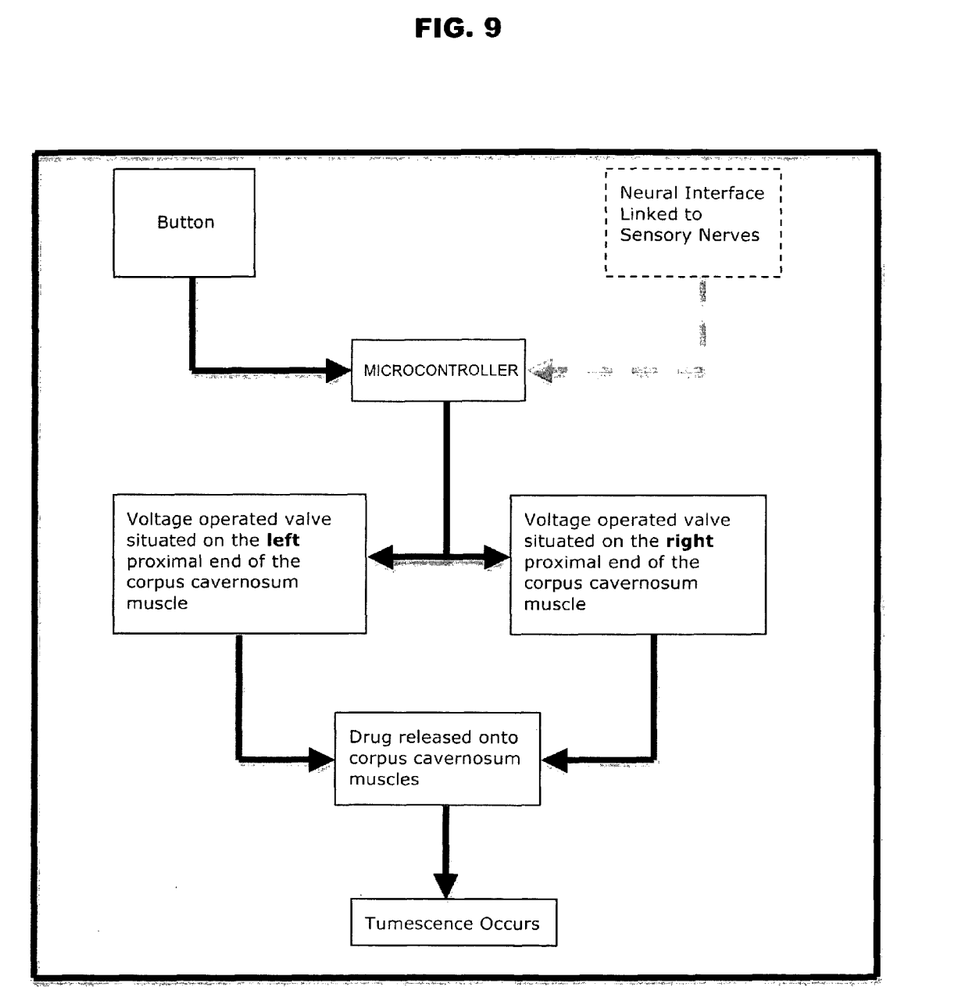
FIG. 9 is a block diagram depicting microcontroller-mediated opening of microfluidic valves in response to an appropriate signal from a user input mechanism in conjunction with neural stimulation.

FIG. 9 provides a flow-chart depicting the operation of the system in an embodiment where the microcontroller is responsive to input from a neural interface only after an appropriate signal (or sequence of signals) is received from a patient input mechanism, in the depicted case, an implanted subcutaneous button.

A patient's dosage may be programmed by the clinician to allow optimization of dosage for each patient, or the dispensed dosage may be preset in accordance with clinical experience. In accordance with known fluid dynamic principles, the dose delivered can be varied by altering the time period during which the microfluidic valves remain open. The proper dosage will be dependent on the selected pharmaceutical, the patient's response to the pharmaceutical, and any other factors the prescribing physician deems relevant. In practice, the flow rate of the constant-pressure pump may diminish slightly over time, as the volume of the propellant chamber increases. Therefore the microcontroller should be programmed to compensate for a decrease in flow rate by allowing for a correspondingly longer duration of valve opening, thereby maintaining the proper therapeutic dosage.

In accordance with the invention, the microcontroller be maintained in a "sleep mode" or low power consumption mode during times where no sexual stimulus is occurring. In one embodiment, the microcontroller will only exit "sleep mode" after registering a neural stimulus above the selected threshold frequency. In an alternative embodiment, the microcontroller will exit "sleep mode" only after appropriate patient input via the input mechanism is registered. In "sleep mode," battery power will be used only to power the patient input, sensory input or both, on the microcontroller. Once a patient input or sensory input is registered, the controller will exit "sleep mode" and divert power to the processor's clock. In one embodiment, the clock is used measure the duration of registered supra-threshold sexual stimulus, in another embodiment, the clock is used to test the timing of any patient-initiated input, such as a sequence of activations of an implanted subcutaneous button; in yet another embodiment, the clock may be used to measure both, either sequentially or simultaneously. Additionally, the microcontroller will enforce a refractory period after each dose administration to prevent overdose. Should a patient be instructed by a physician to engage in sexual activity at a limited frequency, for example, no more than twice in any five-day period, the microcontroller may be programmed so that the refractory period corresponds with such limitation.

In one embodiment, the microcontroller will be remotely programmable by the clinician as to certain operational characteristics, including, but not limited to, the sexual stimulus threshold frequency, the duration of supra-threshold sexual stimulus necessary to trigger drug release, the duration of the forced refractory period, and the drug dosage amount.

Power for the system, used to power the microcontroller, power the patient input mechanism, and to open and close the microfluidic solenoid valves, can be provided, for example, by a 5 volt lithium ion battery or the like. Calculations show that over the course of a decade of typical use, based on the power draw of the low-power microfluidic valves cited above and a standard microcontroller, such lithium ion batteries have sufficient stored energy to power the device. This is similar to the clinically-relevant lifetime for implantable pacemakers, and one of skill in the art would be able to select an appropriate power source similar to those already in clinical usage which meets the performance requirements of the described system. In addition, for extended implanted lifespan, one embodiment of the system may incorporate an induction charging mechanism.

As described above, the system is capable of delivering a highly-regulated precision dosage of a therapeutic directly to the corpus cavernosum. In addition, in a preferred embodiment the drug pump reservoir may be refilled multiple times over the life of the device, and the microcontroller may be reprogrammed by medical personnel to deliver a specified dose that differs from the dose initially selected by the prescribing physician. This results in a system that is highly flexible with regard to the choice of therapeutic for administration. Given the currently-approved therapeutics available on the market, papaverine HCl and phentolamine are excellent choices for use with the described system, although other therapeutics may be used. As new therapeutics are approved for the treatment of ED, they may be found to be equally, or more, suitable for administration via the described system. In addition, a physician may elect to change the drug administered by the system over the course of a patient's treatment. Ideal therapeutic candidates would be highly stable in solution at physiologic temperatures for long periods of time, be effective in minimal dosages, be quick acting, and have minimal side effects. Any suitable therapeutic solution meeting these requirements may be implemented with the described system.

Surgical kits for implantation of the described device may include different undersurface variations for attachment to the housing of the device, a variety of electrode and catheter lengths, as well as electrodes adapted for connecting to either the cavernous nerves or the dorsal nerves. The electrodes may be composed of a metal alloy and insulated with a polymeric insulator, for example, polyurethane. In one embodiment, the distal end of the electrode is fashioned with a shaped tip, adapted to maintain contact with the selected implant location; the proximal end is adapted to enter the device housing and interface with the microcontroller.

A number of implementations have been disclosed herein with respect to the treatment, cure or mitigation of ED. Nevertheless, it will be understood that various modifications may be made without departing from the spirit and scope of the claims, including the use of the disclosed system for the treatment of other ailments. Accordingly, other implementations are within the scope of the following claims.

What is claimed is:

1. An implantable drug delivery system for the treatment of erectile dysfunction, comprising:
   a passively pressurized drug infusion pump containing a therapeutic, one or more catheters,
one or more microfluidic valves,
a microcontroller, and
one or more patient input mechanisms,
wherein one of the one or more patient input mechanisms comprises an implantable neural interface,
wherein the one or more microfluidic valves are under operative control of the microcontroller,
wherein the microcontroller opens the one or more microfluidic valves to dispense a discrete dosage of the therapeutic in response to a signal from the one or more patient input mechanisms,
wherein the implantable neural interface is in electrical communication with nerves associated with a subject's penis, and
wherein the microcontroller is programmed to interpret signals registered by the implantable neural interface, the signal interpretation further comprising requiring that the signals registered by the implantable neural interface exceed a selected threshold stimulus frequency for a defined duration within a predetermined time window prior to release of the therapeutic.

2. The implantable drug delivery system of claim 1 wherein the passively pressurized drug infusion pump and microcontroller are enclosed within a single housing.

3. The implantable drug delivery system of claim 2 wherein the single housing is adapted to be implanted within a subject's abdomen and wherein the implantable drug delivery system is configured to allow one-way fluid communication from the passively pressurized drug infusion pump to a subject's penile tissue via the one or more catheters and one or more microfluidic valves.

4. The implantable drug delivery system of claim 1 wherein the passively pressurized drug infusion pump further comprises: a propellant chamber, a drug reservoir, and a flexible bellows that allows the propellant chamber to exert a pressure on the drug reservoir, wherein the propellant chamber contains a two-phase fluid that has a vapor pressure at body temperature.

5. The implantable drug delivery system of claim 4 wherein the passively pressurized drug infusion pump further comprises a filter and a capillary flow restrictor disposed in a fluid path.

6. The implantable drug delivery system of claim 4 further comprising a drug reservoir fill port and a catheter outlet port arranged on a surface of a housing.

7. The implantable drug delivery system of claim 1 wherein a second of the one or more patient input mechanisms is selected from the group consisting of: an implantable subcutaneous button, an implantable subcutaneous RFID tag, an implantable subcutaneous RFID reader, an implantable subcutaneous capacitive touch sensor, an implantable subcutaneous vibration sensor, and an implantable subcutaneous radio frequency control module.

8. An implantable medical apparatus for the treatment of erectile dysfunction, comprising a passively pressurized drug infusion pump containing a therapeutic that stimulates erection, one or more microfluidic valves, one or more catheters for fluid communication with penile tissue, a microcontroller, and one or more patient input mechanisms, wherein one of the one or more patient input mechanisms comprises an implantable neural interface, wherein the implantable medical apparatus is configured such that a signal received by the one or more patient input mechanisms is transmitted to the microcontroller, which signals the one or more microfluidic valves to switch to an open state, thereby allowing the pressure within the passively pressurized drug infusion pump to propel the therapeutic, via the one or more catheters, to the penile tissue,
wherein the microcontroller is programmed to enter a defined refractory period after each administration of therapeutic, during which refractory period no further administration of therapeutic is permitted regardless of any subsequent signal received by the one or more patient input mechanisms.

9. The implantable medical apparatus of claim 8, wherein the microcontroller is programmed to allow administration of the therapeutic after the refractory period has concluded.

10. A method for the treatment of erectile dysfunction comprising:
implanting a drug delivery system within a body of a patient wherein
(a) the drug delivery system comprises a housing, one or more catheters, one or more microfluidic valves, an implantable neural interface, and one or more additional patient input mechanisms;
(b) the housing encloses a propellant chamber, a drug reservoir containing a therapeutic selected to stimulate an erection, a microcontroller and a power source, and the housing further provides (i) a drug refill port in fluid communication with the drug reservoir and (ii) one or more outlet ports allowing fluid communication between the drug reservoir and the one or more catheters;
(c) the drug delivery system further provides that the one or more catheters each have a proximal end in fluid communication with the one or more housing outlet ports and each has a distal end positioned in fluid communication with a corpora cavernosa of the patient, and wherein the one or more microfluidic valves are situated proximal to the distal end of each of the one or more catheters;
wherein the method comprises implanting the housing, the implantable neural interface and the one or more additional patient input mechanisms within an abdomen of the patient, wherein the one or more additional patient input mechanisms are positioned subcutaneously so that they may register electrical, radio frequency or physical signals from outside the body of the patient;
and wherein the method further comprises the release of the therapeutic in response to a signal received by the implantable neural interface after the one or more additional patient input mechanisms receive a signal from outside the body of the patient, subject to a further condition that the microcontroller is not within a refractory period prohibiting delivery of a dosage of the therapeutic.

* * * * *